United States Patent
Knebel et al.

(10) Patent No.: US 9,116,354 B2
(45) Date of Patent: *Aug. 25, 2015

(54) SPIM MICROSCOPE WITH A STED LIGHT SHEET

(75) Inventors: Werner Knebel, Kronau (DE); Wolfgang Oestreicher, Mannheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 469 days.

This patent is subject to a terminal disclaimer.

(21) Appl. No.: 13/279,013

(22) Filed: Oct. 21, 2011

(65) Prior Publication Data
US 2012/0098949 A1    Apr. 26, 2012

(30) Foreign Application Priority Data
Oct. 22, 2010   (DE) .......................... 10 2010 060 121
Jun. 15, 2011   (EP) ...................................... 11169989

(51) Int. Cl.
G02B 21/16    (2006.01)
G02B 21/00    (2006.01)
G02B 21/06    (2006.01)

(52) U.S. Cl.
CPC .............. *G02B 21/16* (2013.01); *G02B 21/002* (2013.01); *G02B 21/06* (2013.01)

(58) Field of Classification Search
USPC .............................. 250/458.1, 449.1; 850/31; 359/368–398; 348/79–80
See application file for complete search history.

(56) References Cited

U.S. PATENT DOCUMENTS

| | | | |
|---|---|---|---|
| 5,731,588 A * | 3/1998 | Hell et al. ................... | 250/458.1 |
| 7,554,725 B2 * | 6/2009 | Stelzer et al. ................. | 359/385 |
| 7,787,179 B2 * | 8/2010 | Lippert et al. ................ | 359/385 |
| 7,863,585 B2 * | 1/2011 | Hell et al. ................... | 250/459.1 |
| 8,174,692 B2 * | 5/2012 | Hell et al. ...................... | 356/317 |
| 8,362,448 B2 * | 1/2013 | Wolleschensky et al. . | 250/459.1 |
| 8,575,570 B2 * | 11/2013 | Choi et al. .................. | 250/459.1 |
| 2006/0033987 A1 * | 2/2006 | Stelzer et al. ................. | 359/385 |
| 2009/0237765 A1 * | 9/2009 | Lippert et al. .............. | 359/213.1 |
| 2009/0299693 A1 * | 12/2009 | Kane et al. ..................... | 702/179 |
| 2010/0177376 A1 * | 7/2010 | Arnold et al. ................. | 359/307 |

(Continued)

FOREIGN PATENT DOCUMENTS

| | | |
|---|---|---|
| DE | 102007015063 | 10/2008 |
| DE | 102007045897 | 4/2009 |

(Continued)

OTHER PUBLICATIONS

A.H. Voie, et al: "Orthagonal-plane fluorescence optical sectioning: three-dimensional imaging of macroscopic biological specimens", Journal of Microscopy, vol. 170, 229-236 (1993).

(Continued)

*Primary Examiner* — Sath V Perungavoor
*Assistant Examiner* — Dakshesh Parikh
(74) *Attorney, Agent, or Firm* — Schlee IP International, P.C.; Alexander R. Schlee

(57) ABSTRACT

A STED-SPIM-microscope (Selective Plane Imaging Microscopy) having a y-direction illumination light source and a z-direction detection light camera. An x-scanner generates a sequential light sheet by scanning the illumination light beam in the x-direction. By optionally turning on a STED deactivation light beam the light sheet can optionally be made thinner and therefore the optical resolution can be increased.

23 Claims, 8 Drawing Sheets

(56) References Cited

U.S. PATENT DOCUMENTS

| | | | |
|---|---|---|---|
| 2010/0177381 A1* | 7/2010 | Lippert et al. | 359/398 |
| 2010/0201784 A1* | 8/2010 | Lippert et al. | 348/46 |
| 2010/0265575 A1* | 10/2010 | Lippert et al. | 359/385 |
| 2011/0031414 A1* | 2/2011 | Lippert et al. | 250/459.1 |
| 2011/0036996 A1* | 2/2011 | Wolleschensky et al. | 250/459.1 |
| 2011/0186754 A1 | 8/2011 | Dodt | |

FOREIGN PATENT DOCUMENTS

| | | |
|---|---|---|
| DE | 10 2008 009 216 | 8/2009 |
| DE | 102008018476 | 10/2009 |
| GB | 2416453 | 1/2006 |
| WO | 9502139 | 1/1995 |
| WO | 2009100911 | 8/2009 |
| WO | 2009124700 | 10/2009 |
| WO | 2010069987 | 6/2010 |

OTHER PUBLICATIONS

J. Huisken, et al.: "Optical Sectioning Deep Inside Live Embryos by Selective Plane Illumination Microscopy", Science, vol. 305, 1007-1009 (2004).

S. Hell, J. Wichman: "Breaking the diffraction resolution limit by stimulated emission: stimulated-emission-depletion fluorescence microscopy", Optics Letters vol. 19 (11), 780-782.

F. Fahrbach, A. Rohrbach: "Microscopy with non diffracting beams", FOM 2009, Krakau (Abstract).

J. Huisken, D.Y.R. Stainier: "Even fluorescence excitation by multidirectional selective plane illumination microscopy(mSPIM)", Optics Letters, vol. 32, No. 17, 2608-2610 (2007).

* cited by examiner

SPIM MICROSCOPE WITH A STED LIGHT SHEET

CROSS-REFERENCE TO RELATED APPLICATIONS

This application claims the priority of the German patent application DE 102010060121.7 having a filing date of Oct. 22, 2010 and claims priority of the European patent application EP 11169989.8 having a filing date of Jun. 15, 2011. The entire content of this prior German patent application DE 102010060121.7 and the prior European patent application EP 11169989.8 is herewith incorporated by reference.

BACKGROUND OF THE INVENTION

The invention relates to a SPIM-microscope comprising a light source sending an illumination light beam from a y-direction onto an object to be imaged and a camera detecting in a z-direction as a first detection direction light emanating from the object as fluorescent light and/or as reflected light, wherein the z-direction extends substantially perpendicular to the y-direction.

In particular, biological samples should be analyzed both quickly and without damaging the sample. For many applications, it is useful to generate a 3-dimensional image. Scattering artifacts and absorption artifacts should be avoided that may occur due to interaction of the illumination light with the sample, in particular in the field of fluorescence microscopy where the illumination light has the function of an excitation light for exciting fluorescence.

For analyzing microscopic samples fast, without causing damage and with a high resolution the so-called SPIM technology is specifically suitable (Selective Plane Illumination Microscopy) where the illumination light generates a light sheet, while the detection light generated by fluorescence and reflection is detected in a perpendicular direction compared to the illumination direction by a camera.

A light sheet is an illumination volume with a substantially rectangular cross-section that is very thin in a first cross-sectional direction (here the z-direction) and significantly larger in a second cross-sectional direction (here the x-direction) in comparison to the first cross-sectional direction. The illumination direction (here the y-direction) extends substantially perpendicular to the first cross-sectional direction (here the z-direction) and substantially perpendicular to the second cross-sectional direction (here the x-direction). The light sheet is focused by a cylindrical lens and the focus or a focal length of the light sheet is to be understood as a certain range that extends in the illumination direction (here the y-direction) where the light sheet is particularly thin so that the illuminated volume has the shape of a sheet, i.e. is very thin in the z-direction and much larger in the x- and in the y-direction.

Generating a light sheet according to the prior art SPIM technology using a cylindrical lens has the disadvantage that the system is quite unflexible, for instance provides a fixed focus and therefore a predetermined illuminated volume. For achieving a high resolution, a very thin and long focus is advantageous. This focus can be scanned for obtaining a 3-dimensional image in one direction over the sample. Since an increased length also increases the width the resolution in the z-direction is decreased. This means that a long focus that results from selecting a low numerical aperture of the illumination optics has the consequence that also the thickness of the illuminated volume is high. This means that the optical resolution along the optical axis in the detection direction is likewise low. Depending on the practical application the consequence is a conflict of goals: If a high depth of penetration of the illumination light should be achieved, an elongate focus is required that does, however, result in a thicker light sheet and therefore in a lower resolution. An elongate focus is generated with a small numerical aperture of the illumination optics.

Apart from being desirable to achieve at the same time a high depth of penetration for the illumination light while also accomplishing a high resolution, it is generally further desirable to have flexibility in influencing the illumination volume. For example, some applications may require a larger illumination volume, for instance for observing chemical reactions that take place within a specific volume of the object. In contrast to that, also a smaller illumination volume might be desirable, in particular a thinner illumination volume accomplished by a thinner light sheet, for example for having a more clearly defined layer or plane, for instance for determining a diffusion velocity within the object.

SUMMARY OF THE INVENTION

It is an object of the invention to increase the flexibility of the microscope described at the outset, in particular to increase the flexibility in choosing the illumination volume and to increase the flexibility in choosing the type of microscopy that is applied.

According to the present invention, this is achieved by a first x-scanner generating a sequential light sheet by scanning the illumination light beam in an x-direction, wherein the x-direction extends substantially perpendicular to the y-direction and to the z-direction and the light sheet is sequentially formed in a plane that is defined by the x-direction and the y-direction; and a deactivation light source sending from the y-direction at least one deactivation light beam onto the object making the sequentially generated light sheet in the z-direction thinner, wherein the deactivation light beam has in intensity maximum that is at least offset in the z-direction in relation to the illumination light beam and extends in parallel to that illumination light beam that is scanned in the x-direction.

DETAILED DESCRIPTION OF THE INVENTION

According to a preferred embodiment of the invention a deactivation light beam modulator is provided that is adapted to modulate the deactivation light beam such that its cross-section comprises in z-direction at least two intensity maxima with a zero point in between that is provided in the center of the excitation light beam. In the alternative, the deactivation beam can also be modulated so that the side lobes (side maxima) of the deactivation light beam are also deactivated. In this case, it is advantageous if the peaks of the side lobes of the excitation light beam coincide with the peaks of the deactivation light beam. It is possible to modulate the excitation light beam such that stronger side lobes are generated. This allows making the main maximum longer and thinner. Stronger side lobes (side maxima) result in case of non-deactivation in decreasing the resolution in the z-direction. If, however, the side maxima are deactivated, the resolution is increased.

Furthermore, "Tunable Acoustic Gradient Index of Refraction Lenses", in short TAG lenses, can be used, allowing variable options for modulating the excitation beam. Such TAG lenses provide an alternative method for generating a Bessel beam. In such TAG lenses a light refracting fluid is provided within a circular piezoelectric element and is excited by alternating current for generating an alternating index of refraction. Changes in the amplitude and frequency of the excitation signal allow for a fast change of the transmitted pattern. The possible switching speed is determined by the time needed between the switching actions that would allow establishing a stable pattern—which depends predominantly on the viscosity of the fluid. Switching time periods between 300 and 2000 µs are possible for fluid viscosities between 640 cs and 0.65 cs.

According to another preferred embodiment of the invention a phase plate is provided that is adapted to modulate the deactivation light beam. If the deactivation beam should be modulated such that excitation is only narrowed at the sides for generating a thinner light sheet, one single phase plate is sufficient. However, it would in the alternative also be possible to narrow the respective excitation points on all sides, for instance by a vortex filter or a circular phase plate, or two phase plates can be provided and arranged at an angle of 90° with respect to each other for narrowing both in the x-direction (the scanning direction), as well as in the z-direction (thickness of the sequentially generated light sheet).

According to a further preferred embodiment of the invention the excitation light beam modulator can be provided for modulating the excitation light beam into a Bessel beam.

According to another preferred embodiment of the invention the excitation light beam is a Tunable Acoustic Gradient Index of Refraction (TAG) lens. In addition, a multiphoton excitation has the advantage that side lobes of the modulated excitation beam have only an excitation likelihood that is by two powers of 10 lower than in case of exciting with a continuous light (also called continuous wave or CW excitation) and therefore provides less background in the detection. In particular when exciting with continuous light, modulation of the deactivation beam for suppressing the side lobes of the excitation beam can be useful, wherein the deactivation beam can likewise be modulated by means of a TAG lens.

According to another preferred embodiment of the invention the excitation light beam modulator is an Axicon.

According to another preferred embodiment of the invention at least one Acousto Optical Element is provided allowing to modulate at the least the excitation light beam.

According to another preferred embodiment of the invention the Acousto Optical Element is an Acousto Optical Deflector (AOD). By the AOD the illumination beam can be deflected, for instance, for providing the scanning function. Instead of an AOD in the alternative a galvanometer can be provided for providing the scanning function.

According to another preferred embodiment of the invention the Acousto Optical Element is an Acousto Optical Tunable Filter (AOTF) for selecting the wavelength of the excitation light beam and for adjusting the intensity thereof. A particular advantage provided by the AOT at is its double function, namely for adjusting both the intensity as well as the wavelength. In particular the intensity can be controlled within wide limits by an AOTF, namely the output intensity at the output side of the AOTF can be adjusted to almost 100% of the input intensity and can be controlled down to be as low as just a few thousandth of the input intensity.

According to another preferred embodiment of the invention the deactivation light beam comprises a constant wavelength. This has the advantage that a modulation of the wavelength of the deactivation light beam, for instance by means of an AOTF, can be dispensed with. For this purpose, in multicolor fluorescence microscopy preferably such dyes are chosen that have different excitation wavelengths, but can be deactivated with the one and the same deactivation wavelength.

According to another preferred embodiment of the invention at least one intensity controller is provided for selecting the intensities of the excitation light beam and the deactivation light beam.

According to another preferred embodiment of the invention the intensity controller comprises an Acousto Optical Element.

According to another preferred embodiment of the invention a switch is provided that is adapted to switch between a first operational mode that is the normal SPIM mode without adding the deactivation light beam and a second operational mode that is a SPIM-plus-STED-mode where the deactivation light beam is in addition turned on.

According to another preferred embodiment of the invention, the switch is adapted to make a permanent selection between said first and second operational modes.

According to another preferred embodiment of the invention, the switch is adapted to switch automatically at a specific switching frequency between said first and second operational modes.

According to another preferred embodiment of the invention, an image processing unit that separates the detected light detected by the camera in a first detection direction according to the first and second operational mode with the switching frequency into two data streams and generates simultaneously an image according to the first operational mode and an image according to the second operational mode.

According to another preferred embodiment of the invention, an illumination optics is provided comprising an optical zoom that is provided in the beam path of the excitation light beam and comprises lens groups that are moved mechanically with respect to each other for varying the numerical aperture and therefore expanding or shortening the focus of the sequentially generated light sheet, therefore expanding or shortening the length of the field in the y-illumination direction that is illuminated by the light sheet within the object. The illumination optics comprises preferably an illumination objective. By the flexible optical zoom unit the length of the light sheet (in y-direction and in z-direction) can be adjusted. If only a thin layer should be illuminated, the numerical aperture of the zoom optics is increased, having the consequences though that the usable length of the light sheet is decreased. The invention overcomes this conflict of goals by making the light sheet thinner and therefore making the illuminated volume thinner by adding the deactivation by the STED beam, allowing to achieve simultaneously an elongate focus while also having a thin, sequentially generated light sheet. A sequence of images can be shot with an increased resolution along the z-direction. Since the optical parameters of the zoom optics are known, by choosing a suitable image processing only that range can be used and combined providing images of the increased resolution.

According to another preferred embodiment of the invention a photodetector is provided detecting fluorescent and/or reflected detection light emanating from the object into a second detection direction that is opposite to the x-direction. Photodetectors are generally faster than cameras, but fail to provide localization, which, however, is not absolutely necessary since via the multiphoton illumination beam a localization can be accomplished; in particular in case of multiphoton illumination this can be easily achieved since for this type of illumination it is almost precisely known what specific volume within the object is illuminated at any given point in time, so that for signal detection light coming from all possible directions scan be detected.

According to another preferred embodiment of the invention in parallel to the 2-dimensional wide field image that is detected in the z-direction by applying the SPIM technology, also confocally a 1-dimensional image of the object is generated that is a line extending in the x-direction. The 2-dimensional image images that illumination plane that is illuminated by the light sheet as described above and influenced by the zoom optics, while in parallel a so-called x-t-image is generated, i.e. a line image that provides in particular in biological samples information about the movement velocity of particular elements within the object, for example via diffusion of molecules or other cell parts (organelles).

According to another preferred embodiment of the invention a z-scanner is provided moving the object in z-direction so that sequentially several light sheets are generated that are spaced apart from each other in the z-direction and therefore provide several illumination planes, wherein the distance between the respective light sheets and the camera is kept constant. The advantage is that the entire illumination optics as well as the SPIM detection optics and the confocal detection optics that can be turned on optionally in addition remain at the same location and further that the illumination beam does not have to be deflected in the z-direction by a scanner, resulting in a simplified illumination optics. In the alternative, it is however also possible to move the illumination optics or to deflect the illumination beam in z-direction, for instance by means of an Acousto Optical Deflector (AOD) or by means of a galvanometer. In this case, preferably the SPIM detection optics are moved to track the illumination, which can be accomplished by changing the location of the objective of the SPIM detection optics or by displacing the entire SPIM detection optics including the camera.

According to another preferred embodiment of the invention a switch is provided that is adapted to switch between the following operational modes:
i) confocal detection of detection light opposite to the y-illumination direction;
ii) SPIM detection of wide field detection light in the z-direction;
iii) multiphoton detection of wide field detection light in the z-direction;
iv) simultaneous detection of the aforementioned confocal detection and spin detection; and
v) simultaneous detection of the aforementioned confocal detection and multiphoton detection.

According to another preferred embodiment of the invention the operational modes i)-v) can optionally be established with or without additionally turning on the STED deactivation beam. Turning on or off can be performed linewise or even pixelwise and the data streams can be separated. This allows to generate two different images imaging different illumination volumes. These images can also be combined by an overlay, for instance for observing chemical reactions within a larger illumination volume, but simultaneously also for detecting diffusion velocities within a smaller illumination volume but at a higher precision as for instance possible via 2-dimensional FCS (Fluorescence Correlation Spectroscopy).

BRIEF DESCRIPTION OF THE DRAWINGS

The invention is discussed in the following by referring to the drawings. In the drawings show.

DETAILED DESCRIPTION OF THE DRAWINGS

Figure 1:
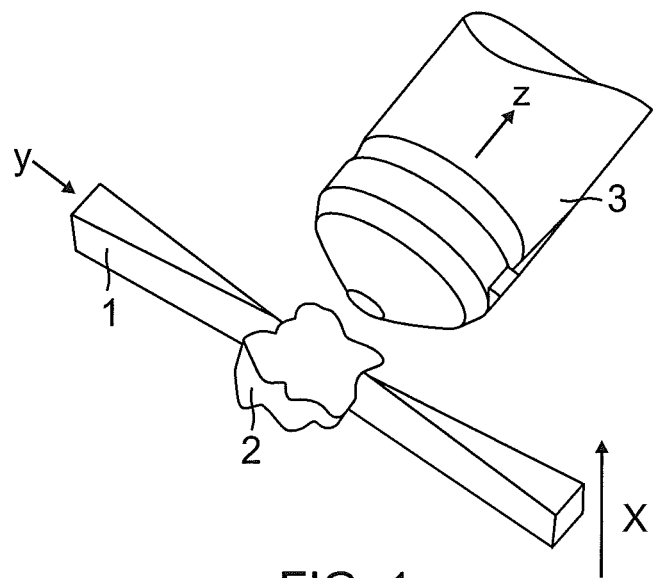
FIG. 1 a schematic perspective view of the basic principle of the SPIM-technology according to the prior art.

FIG. 1 shows in a simplified fashion the principle of a SPIM-microscope according to the prior art, operating based on the "Selective Plane Imaging" technology principle. Illumination is performed in the y-direction by a light sheet for illuminating the object in a specific object plane. The detection direction extends substantially perpendicular to the light sheet 1, i.e. in z-direction, wherein the detection of the detection light is performed by an objective 3. As shown in FIG. 1, the light sheet 1 should be specifically thin over a range of the inner section for obtaining a high a resolution in the z-direction. A high resolution is accomplished if the light sheet 1 comprises a narrow focus within the object.

As will be explained below in more detail, the length of this focus can be influenced, making the imaged field larger, but decreasing the sharpness of the focus and therefore decreasing the narrowness of the light sheet 1 and therefore decreasing the resolution of the picture in the z-direction. Depending on the specific application, it might be useful to have less resolution in the z-direction but at the same time view a larger field and a larger imaging volume based on a thicker light sheet. A larger imaging volume might also be useful if the generated image still allows to view the aspects of interest of the image well, but at the same time allows for a larger imaging volume having the advantage that it is easier to ascertain that the imaged volume does indeed contain the aspect of interest. If an image of an even higher resolution should then be generated of the aspect of interest it is possible to manipulate the focus of the sequential light sheet 1 by the zoom-optics to make the focus smaller but sharper.

In contrast to confocal scanning microscopy, detection of the detection light in the z-direction according to the SPIM-technology requires localization of the detected light since the SPIM-technology is a wide-field microscopy technology. The localization is typically accomplished by a camera, for instance a CCD-camera or a CMOS-camera. If a 3-dimensional image of an object should be generated by the SPIM-technology, the light sheet 1 or the object can be scanned in z-direction and the images obtained in the various illumination planes can be combined to generate a 3-dimensional image. This image processing is also named "Rendering", in this case in the z-direction.

Figure 2:
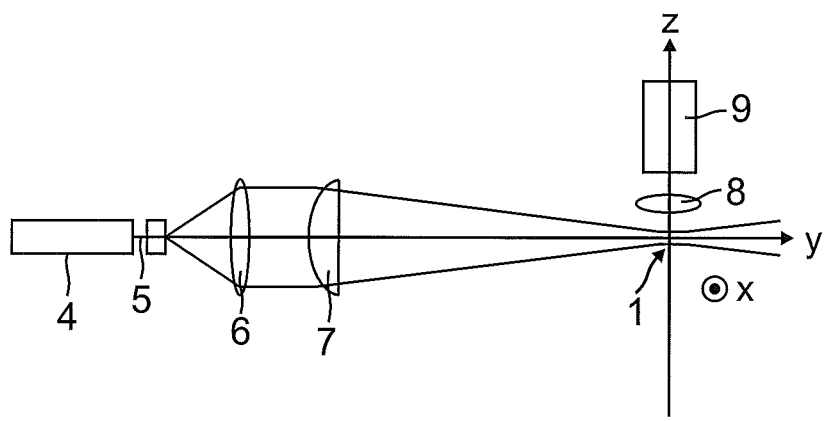
FIG. 2 a schematic view of the illumination beam paths and the detection beam paths according to the SPIM-technology according to the prior art.

FIG. 2 shows schematically an illumination beam path according to the prior art in a SPIM-microscope. A laser 4 generates an illumination beam 5 that is sent through a beam expander into the collimating lens 6 that is succeeded by a cylindrical lens 7 focusing the light sheet 1 onto the object. An objective lens collects the detection light and directs it into a camera 9. The focus of the light sheet can be influenced by moving elements in the group of lenses, in this strongly simplified example according to FIG. 2 by moving the cylindrical lens 7 in relation to the collimating lens 6.

According to the invention, the light sheet 1 can be narrowed further by turning on in addition a STED deactivation beam (Stimulated Emission Depletion), i.e. can be made thinner for accomplishing a higher resolution in the z-direction.

Figure 3:
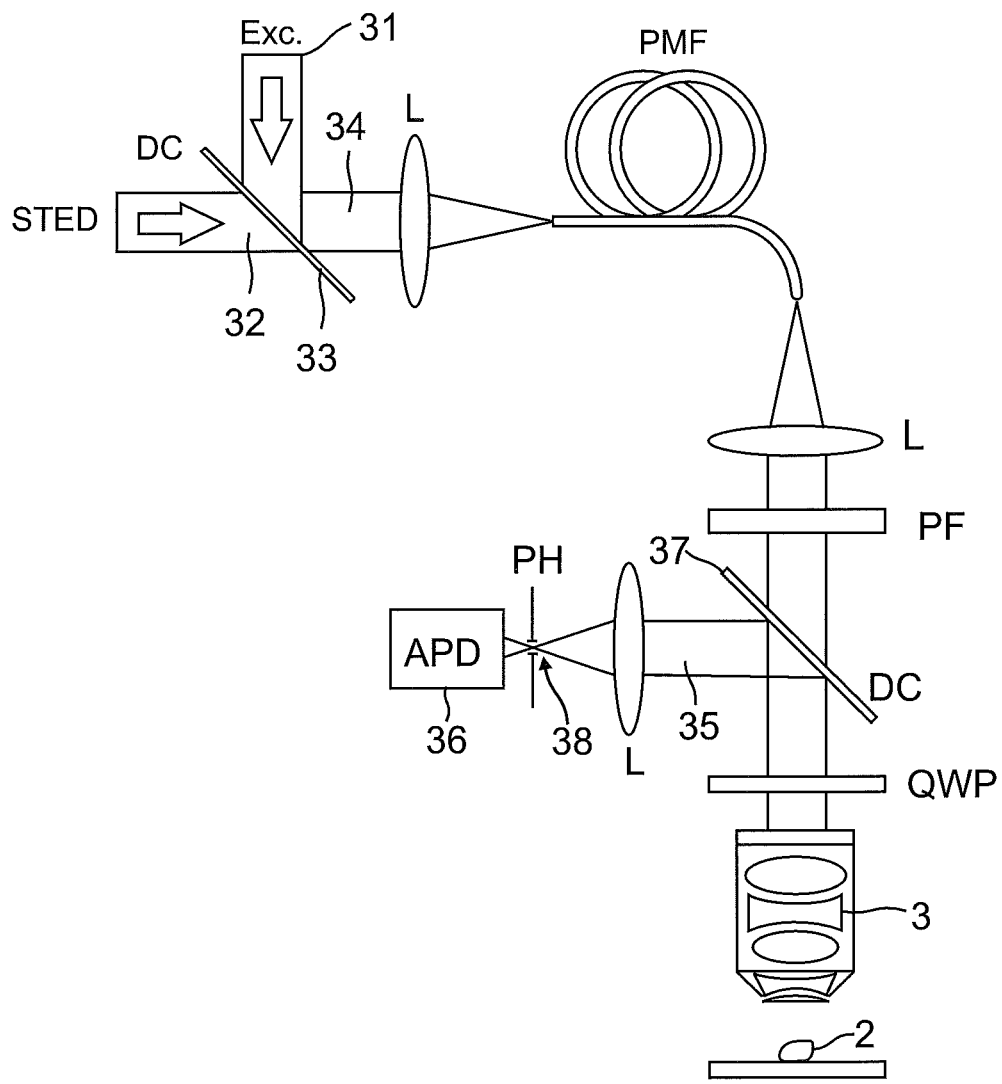
FIG. 3 a schematic view that also demonstrates the STED-principle according to the prior art.

The basic structure of a STED microscope as it is known from the prior art is shown in FIG. 3. An excitation beam 31 and a deactivation beam 32 are combined by a beam combiner, in this embodiment for example by a dichroic filter, to a joint beam path 34 that is directed through an objective 3 onto the object 2. Several other optical elements can be provided in between, for instance lenses, light conducting fibers or color filters. The deactivation beam is typically modulated in its intensity distribution, which can for instance be accomplished by phase plates, as described below by referring to FIG. 5, but can also be achieved by lenses specifically structured for that purpose. The modulation can be performed in that the deactivation beam has a zero point in its center, meaning that the intensity is zero or very low in the zero point while around this zero point a uniform, ring-shaped intensity maximum is provided. The dyes which are used in fluorescence microscopy react on specific excitation wavelengths and deactivation wavelengths allowing to excite fluorescence or to deactivate fluorescence specifically well. Typically, an excitation wavelength and a deactivation wavelength differ from each other and the excitation beam and the deactivation beam are sent in a time-delayed manner with respect to each other onto the object. This is referred to as pulsed STED, but it has also been discovered that hybrid versions are possible.

Pulsed excitation with delayed pulsed deactivation
CW (Continous Wave) excitation with CW deactivation
Pulsed excitation with CW deactivation
Pulsed MP (multiphoton) excitation with pulsed deactivation
Pulsed MP (multiphoton) excitation with CW deactivation By exciting, an image point of a specific size can be excited to emit fluorescent light, while immediately thereafter around the center of excitation a deactivation can be applied, allowing to narrow down the fluorescent light emitted from this image point of the object 2 to a small image point and therefore allowing to increase the resolution. For multi-color fluorescence microscopy a variety of different dyes can be used distinguishing from each other by different excitation wavelengths, i.e. excitation light of a variety of wavelengths that allow a specifically strong excitation for emitting fluorescent light. Preferably, the combination of dyes can be chosen such that these can be deactivated by a common, same deactivation wavelength so that it can be avoided having to provide a variety of deactivation wavelengths.

The detection light 35, which is sent from the object back through the objective 3, can be sent by a beam splitter, in this case likewise a dichroic mirror 37, through a lens and a suitable aperture 38 for eliminating scattered light onto a photodetector 36.

In the example shown in FIG. 3 demonstrating the basic structure of a STED-microscope the excitation beam and the deactivation beam are combined to a joint beam path. The detection beam path extends over a certain range coaxially to but in opposition direction with respect to the excitation light beam and the deactivation light beam up to point where the detection beam is coupled out to the side by the dichroic mirror 37 towards the photodetektor 36. This arrangement is particularly compact, but it should be understood that the deactivation beam can also be sent through a separate deactivation beam optics, allowing a more flexible modulation of the deactivation beam independently from the illumination optics.

Figure 5:
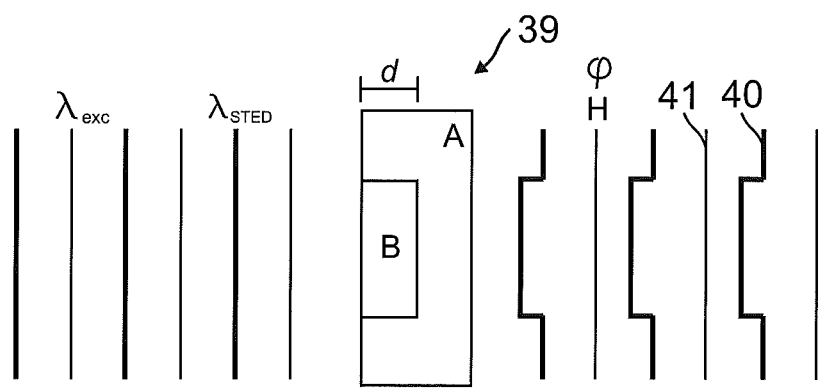
FIG. 5 is schematic view demonstrating the modulation of the STED-deactivation beam by a phase plate.

Modulation of the deactivation beam 40 by a phase plate 39 is demonstrated in FIG. 5. Both the phase as well as the intensity distribution can be modulated with such phase plates 39. For this purpose, the phase plate is designed such that the deactivation beam 40 is modulated, but not the excitation beam 41, i.e. the modulation depends on the wavelength which differs for the deactivation beam 40 in comparison to the excitation beam 41.

Figure 4:
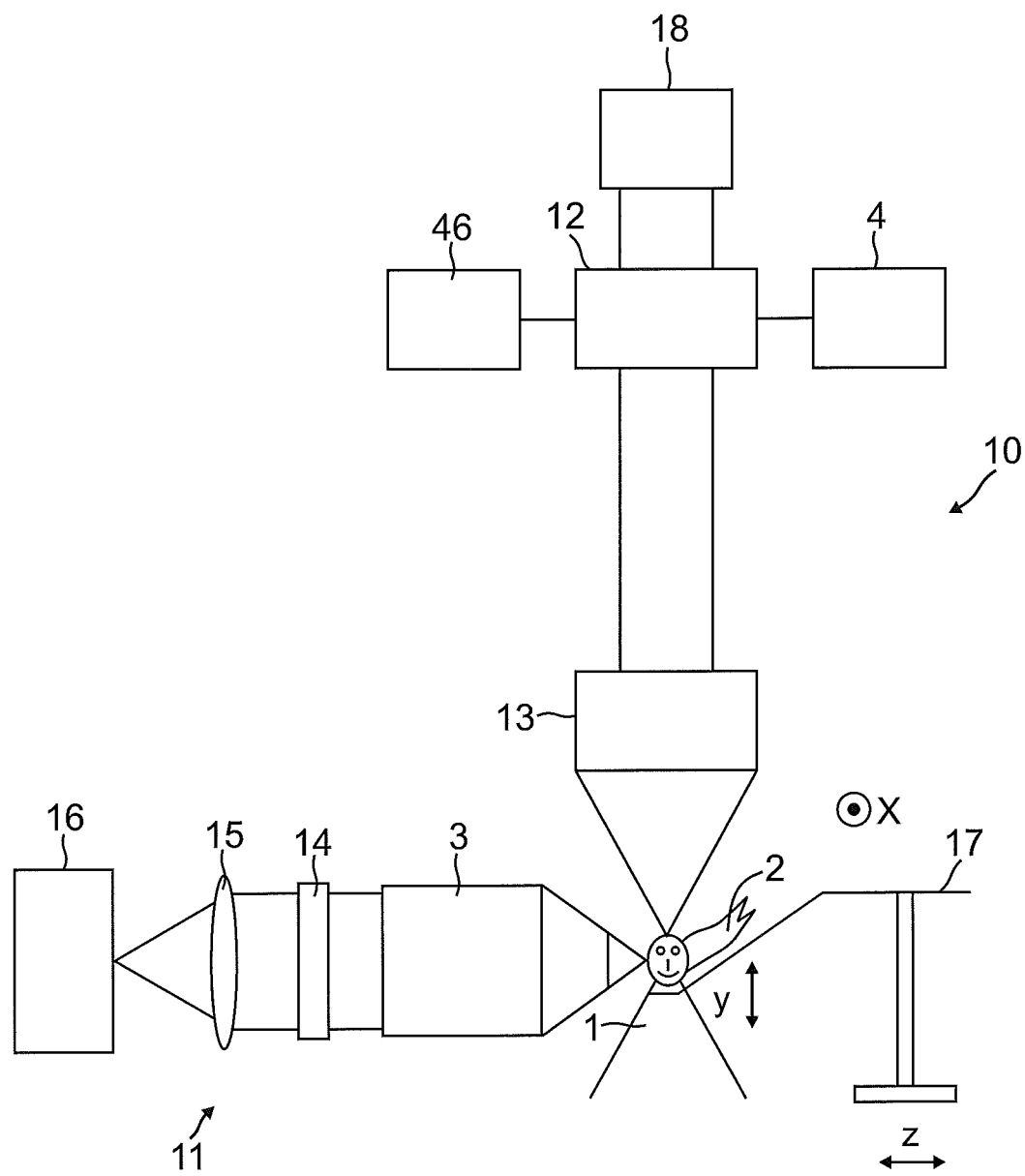
FIG. 4 a schematic view of the microscope according to the invention.

FIG. 4 shows the schematic structure of the SPIM-microscope according to the invention, having an illumination beam path denoted by reference numeral 10 and a SPIM-detection light beam path denoted with the reference 11. The illumination optics beam path 10 comprises in addition the function of a confocal detection light beam path, but extending in the opposite direction compared to the illumination direction.

First of all, the illumination optics beam path is described; a laser 4 generates illumination light that is sent via a scanner 12 into the zoom optics 13. The scanner 12 generates a sequential light sheet 1 for illuminating the object 2. For sequentially generating the light sheet 1 the illuminating laser beam is scanned in the x-direction, i.e. according to FIG. 4 out of the drawing plane or into the drawing plane, respectively. The laser beam may for example have a circular cross-section, but may in the alternative also be modulated in its cross-sectional shape, for instance have an oval cross-section, wherein the longer axis of the oval cross-section extends in the x-direction. Likewise, the illumination beam path can for example be rectangular or may have any other optional shape.

The SPIM-detection light beam path 11 extends in the z-direction, i.e. substantially perpendicular to the y-direction in which the illumination beam path 10 extends. It may be advantageous to deviate slightly from the perpendicular relationship between the illumination beam path and the detection beam path, for instance smaller or larger angles than 90° between the two beam paths can be chosen, for instance for creating background illumination for parts or particles within the object. It is also possible to detect images from different angles and then combine these, as for instance known as mSPIM technology. In the following, for keeping the description simple, a rectangular relationship is described, but should be understood as also encompassing deviating angles which are however to be understood as more or less close to 90°. The detection light emanating from the object 2 either due to reflection or fluorescent light emission is collected by the objective 3. Particularly for multi-color detection a color filter 14 is provided downstream of the objective and is capable of filtering out detection light of specific wavelengths which is then directed via a tubular lens 15 to a camera 16, for instance a CCD—camera 16.

An additional laser 46 is provided generating deactivation light of a specific wavelength. The wavelength of the deactivation light distinguishes from the wavelength of the excitation light. Typically, the deactivation light comprises a longer wavelength than the excitation light. For multi-color microscopy dyes are chosen that have different excitation wavelengths, but approximately the same deactivation wavelength. This has the advantage that for generating the deactivation wavelength only one single laser has to be provided that generates exactly that deactivation wavelength, and a modification of that wavelength is not necessary, allowing to dispense with the expenditure for the wavelength modification, for instance dispense with an Acousto Optical Element (AOTF) and respectively dispense with a frequency generator for driving the AOTF. For STED about 20 dyes are known, for mentioning an example, excitation at a wavelength of 590 nm and deactivation at a wavelength of 600 nm, or excitation at a wavelength of 440 nm, deactivation at a wavelength of 532 nm are known. Both the excitation as well as the deactivation can be adjusted as to frequency as well as to intensity by an AOTF.

Figure 6:
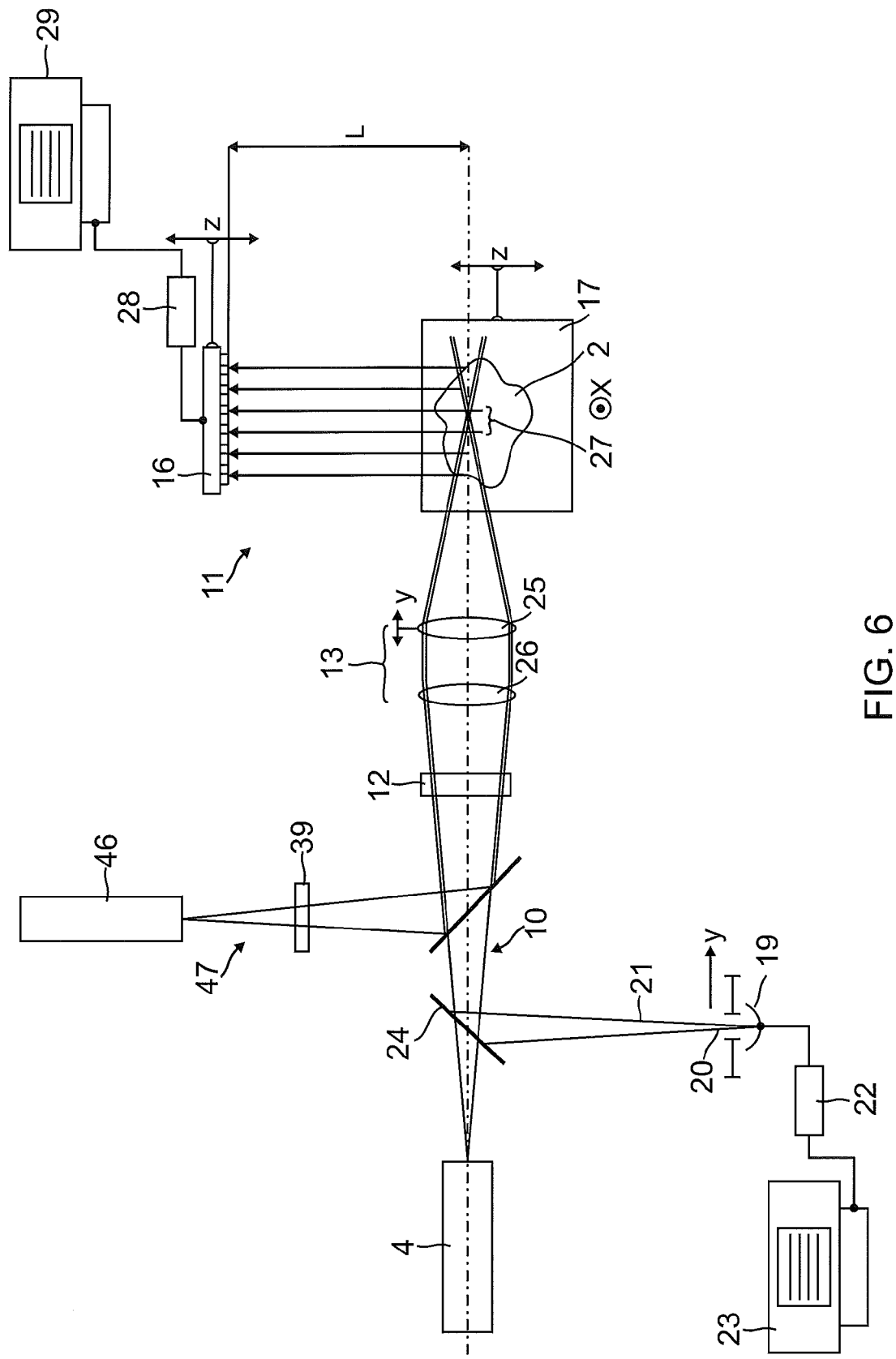
FIG. 6 a schematic view of the microscope according to the invention as shown in FIG. 4 but viewed in the x-scanning direction, including the excitation beam, deactivation beam, and the detection beam paths.

As already discussed above in connection with FIG. 3, the deactivation light can either be sent via the same optics as the excitation light, i.e. follow the same beam path, or can be sent via a separate beam path, as for instance shown in subsequent FIG. 6. In the embodiment according to FIG. 4 the laser 4 generates the excitation light and the laser 46 generates the deactivation light and scans it via a joint scanner 12.

For generating a 3-dimensional image the object carrier 17 can be scanned in the z-direction for illuminating sequentially different illumination planes within the object 2, each of the illumination planes being scanned by a scanned laser beam that is scanned in the x-direction and therefore illuminated by a sequentially formed light sheet 1 that is sequentially formed in the respective illumination plane. A plurality of in the z-direction adjacent sequentially formed light sheets 1 can be combined by "Rendering" in the z-direction.

In case 3-dimensional images should be generated by "Rendering" with a z-drive, moving the object 2 has the advantage that the distance between the respective adjacent illumination planes within the object and the objective remains the same since neither the location of the illumination beam is changed nor the location of the camera 16. In the alternative it is possible to scan the light sheet 1 in z-direction, for instance by a galvanometer. This requires though that the objective 3 is also moved so that the distance between the respective illumination plane and the object remains the same. In the alternative, it is of course possible to move the entire SPIM detection optics comprising the objective 3, the filter 14, the tubular lens 15 and the camera 16.

The illumination detection optics beam path 10 may as already mentioned further have the function of a confocal detection light beam path, for which purpose the detector 18 can be provided detecting light reflected from the object in the y-direction and/or detecting emitted fluorescent light. Simultaneously with image detection via the SPIM technology through the detection light beam path 11 it is also possible to perform confocal image detection in parallel since the light sheet 1 is generated sequentially by scanning in the x-direction. The confocally generated image is one dimension lower compared to the image detected by the SPIM-detection. If for instance only a 2-dimensional image is generated by the SPIM-detection, i.e. an image within only one single image plane, it is also possible to detect a so called x-t image, i.e. a 1-dimensional line image. This can for instance be used for determining the diffusion speed of specific molecules, that may be marked by a marker or are dyed for emitting fluorescent light, while the 2-dimensional SPIM-image that is imaged simultaneously may provide different information, for instance information which molecules combine to which other molecules in the imaged imaging plane of the object.

The same applies if by means of the SPIM-detection a 3-dimensional image with a z-drive is generated, i.e. that a confocal 2-dimensional image is generated. In this fashion it is for instance possible to determine which molecules combine within the object in the 3-dimensional shape with which other molecules, while in parallel the diffusion speed of molecules diffusing through specific planes can be determined. The simultaneous detection of a SPIM-image with the dimension "n" and a parallel confocally generated image with the dimension "n−1" allows in combination additional determinations, for instance the additional speed information allows to determine which individual elements, for example molecules or other elements, move within the object 2. In particular in the field of microscope this finds new applications within living organisms.

FIG. 6 shows an additional embodiment of the invention. Similar elements are designated with the same reference numerals as in the preceding figures. Also in this figure the SPIM detection light beam path is denoted by the reference numeral 11, while the illumination beam path is designated with the reference numeral 10. Also in this embodiment according to FIG. 6 the illumination beam path 10 has the function of the additional detection beam path wherein the signal detection is performed by means of a photodiode 19 receiving through an aperture 20 confocally detection light 21, and sends a respective signal via the image processing unit 22 into a monitor 23. The detection light is deflected by dichroic mirrors 24 to a photodiode 19. Instead of the photodiode 19 also other light sensors, for instance Avalanche diodes, photomultipliers or a camera can be provided. Since this relates to confocal image detection, no localization is necessary since the information about the location comes from the scanned illumination beam, i.e. it is known which image point of the object is illuminated at a specific point in time, and therefore the information is known that the signal received from that specific image point is from that image point that has been illuminated immediately prior to receiving the signal. Therefore, the expenditure for a camera is not necessary for confocal detection.

For changing the focus of the sequentially generated light sheet 1 a zoom lens 25 may be moved in the y-direction in relation to a further lens 26. For practical applications, a lens group will be provided for this purpose; however, for simplification the discussed embodiment is demonstrated with only 1 single zoom lens 25. The zoom optics 13 in combination with the illumination objective (macro objective) therefore provides an optical zoom allowing to modify the length of the focus range 27. The sharper the focus, the shorter the usable focus length, but at the same time the thinner the light sheet 1. For simplification, the details of the SPIM-detection optics have been omitted in FIG. 6, as these optics have already been shown in FIG. 4 comprising the objective 3, the filter 14 and the tubular lens 15. The schematically shown CCD-camera 16 provides for localization station in the x-y-plane for the detection light received in the z-direction. Via the SPIM image processing unit 28 the signals received by the CCD camera are processed and forwarded to the SPIM monitor 29. If a number of planes should be illuminated within the object 2 the object carrier 17 can be moved in the z-direction. As it can be clearly understood from the illustration according to FIG. 6 the length L meaning the distance between the illumination plane and the CCD-camera always remains the same. As already explained in connection with FIG. 4, it is also possible to move the illumination beam in z-direction while keeping the object 2 at the same location, and by moving instead the CCD-camera, or as this might be easier to implement, to change the position of the objective 3 in relation to the CCD camera 16.

The deactivation light beam that has been generated by the laser 46—this beam is also called STED-beam—has according to this embodiment been sent via a separate deactivation beam path 47. In a similar fashion as the illumination beam also the deactivation beam is at first expanded and then focused by a joint zoom optics.

Via a dichroic mirror in front of the scanning module 12 the beam path of the deactivation light beam is then deflected so that the deactivation beam path extends coaxially to the excitation beam path. The modulation of the deactivation beam is accomplished via the phase plate 39 that has already been described above in connection with FIG. 5. The type of modulation of the deactivation beam is described in more detail below by referring to FIGS. 8a and 8b.

Figure 7:
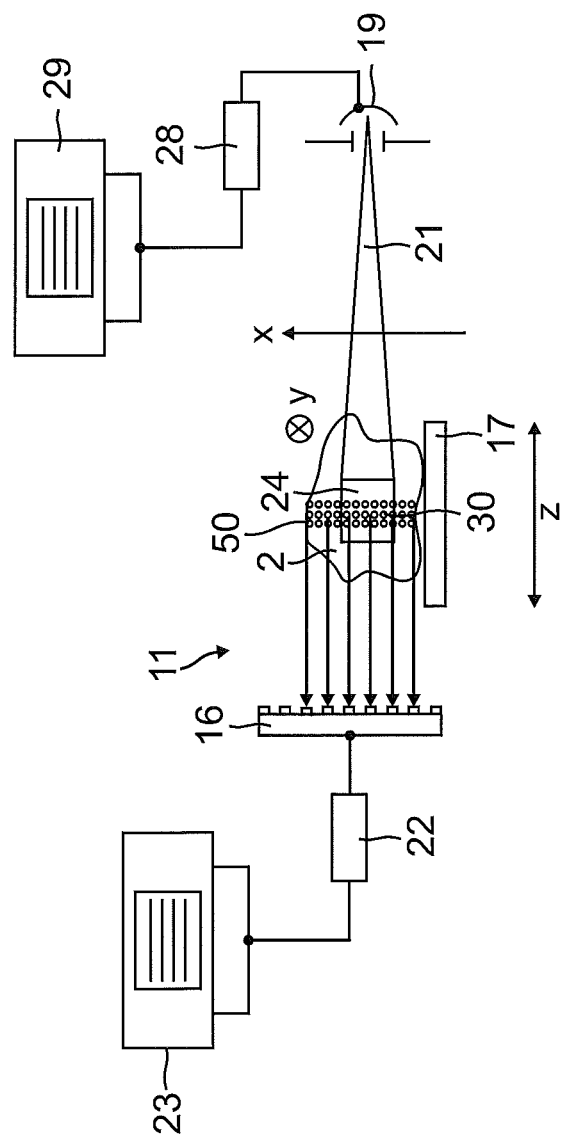
FIG. 7 a schematic view of the microscope shown in FIG. 6, but viewed in the y-illumination direction.

FIG. 7 shows the embodiment illustrated in FIG. 6, but as viewed from a different viewing point, namely in direction of the illumination beam, i.e. viewed in the y-direction. Illustrated are here in particular the individual illumination points 30 which are scanned in the x-direction for generating a sequentially formed light sheet 1, as well as the deactivation points 50 that are sent onto the object by scanning the deactivation points in a row in parallel to the illumination points likewise in the x-direction. The dichroic mirror 24 deflects the detection light in direction of the photodiode 19. The object carrier 17 can be scanned in the z-direction, i.e. can be moved towards the CCD-camera 16 or moved away from the CCD-camera for illuminating different illumination planes within the object.

It would also be possible to generate the excitation beam and the deactivation beam with only one single laser 4 (white light laser). For this purpose, the beam is split to send one part of the beam through an Acousto Optical Element as for instance an Acousto Optical Tunable Filter (AOTF) where the desired wavelength can be selected. By using pulsed lasers a time delay between the excitation beam and the deactivation beam can be implemented by a so-called delay stage.

Figure 8A:
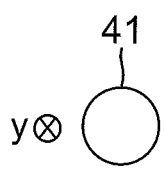
FIG. 8a the cross-section of an excitation beam as well as the related intensity distribution with the coordinates x, y and z.
Figure 8A:
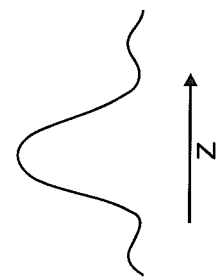
Figure 8B:
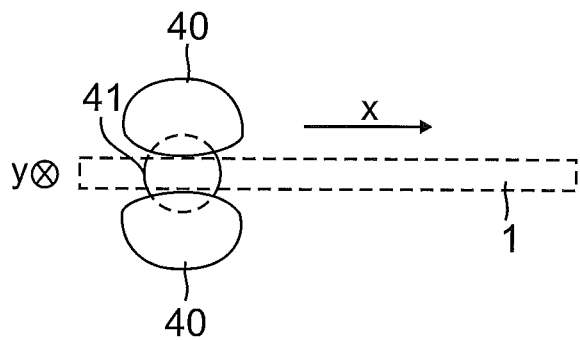
FIG. 8b the excitation beam plus the deactivation beam compared to each other as well as the sequential light sheet generated by scanning in x-direction together with the related intensity distribution with the coordinates x, y and z.
Figure 8B:
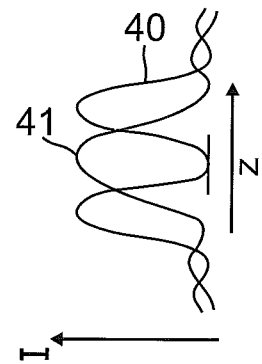

The relationship between the excitation light beam and the deactivation light beam is shown in FIGS. 8a and 8b. FIG. 8a shows the cross-section of a circular excitation beam 41. The directions x, y and z, as shown in FIGS. 4 and 5, are also shown in the FIGS. 8a and 8b. An intensity distribution profile of the excitation beam is shown on the right side, and typically follows a Gauss distribution—apart from relatively small side lobes due to diffraction. FIG. 8b shows a deactivation beam 40 that is modulated such that it comprises on both sides of the deactivation beam 41 an intensity maximum with a zero point in between where the intensity is zero or at least very low. As it can be seen in FIG. 8b, the intensity maxima of the deactivation beam 40 which intensity maxima are provided on both sides of the zero point do not have a circular cross-section, but comprise a cross-section having a flattened curvature towards the center in comparison to the side facing away from the excitation center. As the sequentially generated light sheet 1, which is demonstrated in FIG. 8b in interrupted lines, only a small band in the center area remains in which the deactivation light does not deactivate fluorescence. At the right side next to the cross-section of the excitation beam 41, deactivation beam 40, and sequentially generated light sheet 1, the intensity distributions of the Intensity I of the excitation beam 41 and the deactivation beam 40 are demonstrated on the right side in FIG. 8b.

From FIG. 8b another advantage of the invention becomes apparent, namely that in contrast to the prior art confocal STED-microscopy it is not necessary to border the illumination point all around for obtaining an effective deactivation, but it is only necessary to border the illumination point on each side for making the sequentially generated light sheet thinner. This allows a simplified modulation of the deactivation beam, which can for instance be accomplished by only one single phase plate 39 as shown in FIG. 5.

According to one particular embodiment it is also possible to make the light sheet only on one side thinner by applying the deactivation beam. By specific modulation of the deactivation beam a unilateral deactivation beam profile can be generated that comprises a steep flank on one side and an intensity minimum, the latter preferably in the area of the maximum of the excitation intensity. Other cross-sectional shapes like oval or kind of rectangular may also be advantageous for a one-sided deactivation beam.

It is to be understood that in the alternative also an all around deactivation can be performed, which can be accomplished by a donut shaped deactivation beam that can for instance be generated by a vortex filter with a circular phase plate. This has some advantages if in parallel to the SPIM signal detection at an angle of 90° to the illumination direction also a confocal detection in the opposite direction compared to the illumination direction is performed—as it has been discussed above.

The STED-deactivation beam can be selectively in addition turned on or it can be turned off, which can also be performed just per line or per pixel in x-direction. Since the information is known when the deactivation beam is turned on or is turned off, the respective data streams can be separated, i.e. into a first data stream for generating an image based on the thicker light sheet and respectively covering a larger illumination area (compared to the cross-section of the illumination focus) and a larger illumination volume, and a second data stream for generating an image based on thinner light sheets with a smaller illumination area (in relation to the cross-section of the illumination focus) and a smaller illumination volume. This allows to generate simultaneously in the z-direction a high resolution image by adding the STED-beam, and in z-direction an image of a lower resolution without adding the STED-beam, but with the advantage of illuminating a larger volume within the object.

Independently of adding or turning off the STED-beam, this microscope allows to generate in parallel simultaneously a SPIM-microscopy image of the dimension n and a confocally generated image of the dimension n−1, while these images can also be in parallel generated in the z-direction with the high resolution or a lower resolution by additionally turning on or by turning off the STED-beam, respectively. In total, it is possible to generate simultaneously 4 separate data streams generating the following sets of data:

i) 2-dimensional image (SPIM) at a high resolution, but imaging a smaller volume of the object;
ii) 2-dimensional image (SPIM) at a lower resolution, but imaging a larger volume of the object;
iii) 1-dimensional confocal image x-t in z-direction at a high resolution; and
iv) 1-dimensional confocal image x-t in z-direction at a lower resolution.

The number of light sheets in z-direction is not dependent on the x-dimension, i.e. it is possible to choose from different image formats, for instance the number of pixels in x-direction of 512, while the number of pixels in the z-direction can be more or less. For obtaining a continuous data set in the z-direction without gaps, the feed motion in z-direction must be chosen such that always some overlap is guaranteed (Nyquist Theorem).

Figure 9:
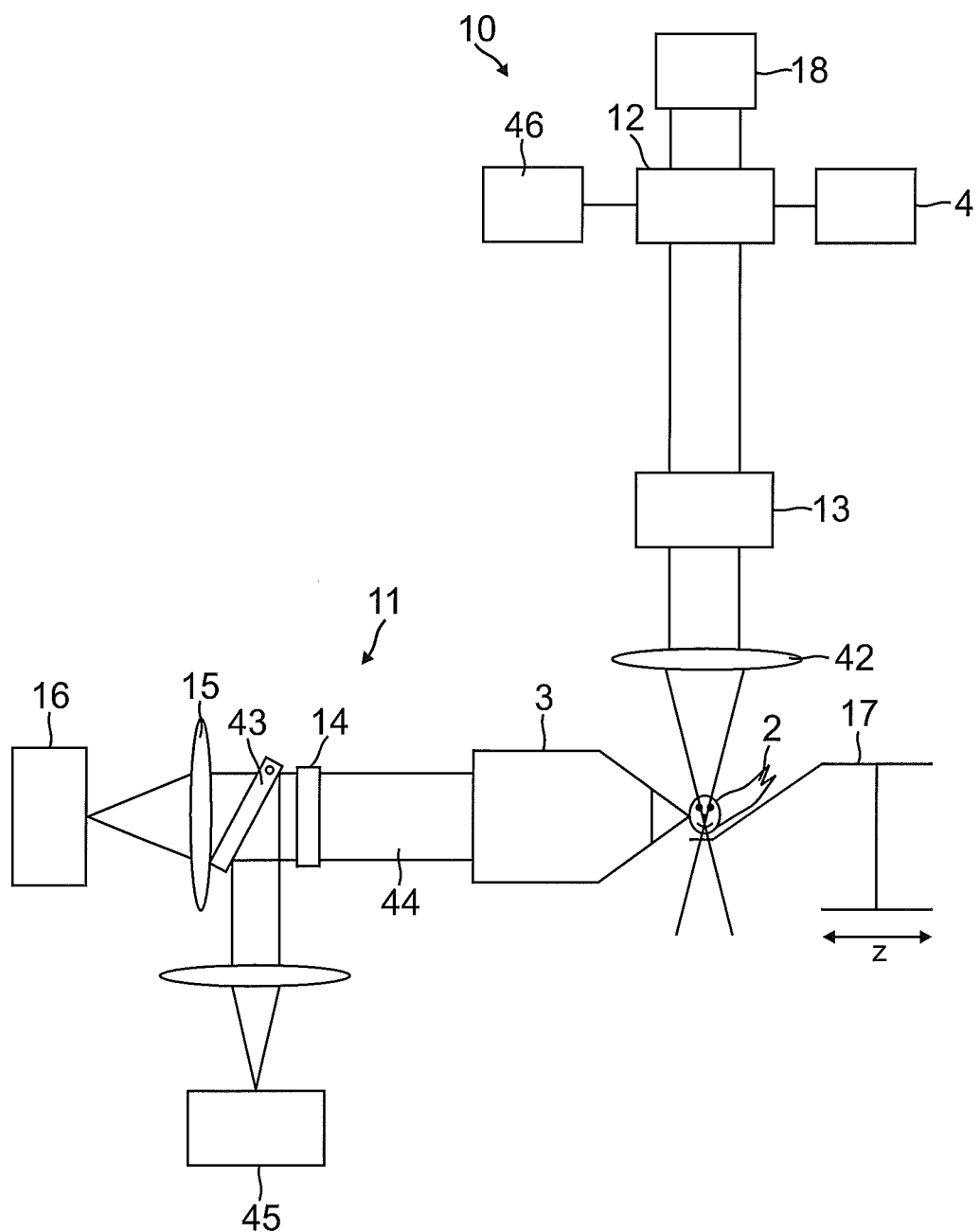
FIG. 9 a schematic view of an additional embodiment of the invention, using the SPIM-detection optics in addition for detecting a multiphoton signal.

FIG. 9 shows an additional embodiment of the invention where the same component parts in comparison to the embodiment according to FIG. 4 are denoted with the same reference numerals. In addition, an illumination objective 42 is provided that can be provided in addition to the zoom optics 13. The illumination objective can also be part of the optical zoom, as for instance in the example according to the embodiment shown in FIG. 6.

In contrast to the illumination with a continuous laser (continuous wave CW) also a pulsed laser can be used for multiphoton fluorescence microscopy sending exciting photons of a long wavelength and of a relatively low energy which is therefore specifically suitable for avoiding damage to the sample, which may particularly be important for biological samples. Like the detection of the SPIM-signal also a multiphoton signal can be extracted by means of a switchable mirror 43 from the detection beam path 44 extending in the z-direction and can be detected by a photomultiplier or an Avalanche photodiode 45. Other than that, the SPIM-signal can be detected by the camera 16 as already described with reference to FIG. 4.

If the camera 16 works fast enough, as a further variation of the embodiment shown in FIG. 9, the switchable mirror 43 can be dispensed with and instead the camera 16 can be used for detecting the multiphoton signal. Since in case of a multiphoton illumination together with detecting the signal in z-direction, i.e. perpendicular to the direction of illumination, for each illumination point on the object a line is imaged onto the camera 16, and by scanning in the x-direction, sequentially a scan-line on the object that extends in the x-direction, an area is sequentially illuminated on the camera 16 that needs to be reduced by software reducing the data back to a line. By scanning in z-direction sequentially several lines of the object can be detected and further processed to an image of an area of the object.

In simple words, this variation of the SPIM signal detection structure is used for a multiphoton signal detection, which is possible with fast cameras, for instance cameras that can detect up to 1000 images per second in the format 512×512.

A specific advantage of the SPIM signal detection structure for the multiphoton signal detection is a significantly increased signal strength, among other reasons due to the following reasons: For generating light sheets typically illumination objectives of a low numerical aperture are used, for instance objectives with a numerical aperture in the range of 0.04 NA. If now the SPIM detection path is used for detecting generated signals from the multiphoton illumination, significantly higher signal strengths can be obtained since the used objectives provide for a much higher numerical aperture (NA) (for instance 1.0 NA). This means gaining signal strength by more than a factor 20.

If the SPIM detection beam path (in z-direction) is used for detecting fluorescent light and the light is sent to a photomultiplier or an APD or APD array or according to the variation described above directly sent to a fast camera, a much higher efficiency can be reached as by using the illumination optics for signal detection in the y-direction, since typically the used numerical aperture of the illumination system is lower than the numerical aperture of the detection system of the SPIM arrangement.

Using multiphoton detection has several advantages. Almost exclusively only those fluorochromes are excited that are in the focus, since excitation requires several photons to arrive more or less simultaneously, which happens almost exclusively in the focus, or put in other words, the likelihood of exciting outside the focus is very low. Another advantage is the higher penetration depth when using wavelengths in the IR range (scattering is low). Another advantage is that no pinhole is necessary, since the entire emitted light can be allocated to the illumination focus. This allows also collecting light from all directions. In contrast, confocal microscopes require that scattered and deflected light needs to be suppressed, which reduces the signal strength. Apart from all these advantages in having a higher signal strength the illumination intensity is lower and therefore avoids damage to the sample, while this solution further provides the structural advantage that the already provided for detection optics of the SPIM-microscope can be used for the multiphoton signal detection, allowing all these advantages without further structural expenditure and only relatively low expenditure on software.

By applying the STED technology it is further possible to increase the high resolution provided by multiphoton illumination even further, i.e. to achieve an increased resolution in the detection direction from about 300 nm in the multiphoton mode up to a resolution of only a few nm in the multiphoton-plus-STED mode. Put in different words, a synergistic effect can be accomplished by the increased signal strength provided by the SPIM detection optics in combination with the high resolution provided by the multiphoton mode plus an additional increase in resolution by applying STED. The specific structural advantage provided by the invention is that three substantively different categories of microscopes can be combined into one single arrangement, namely a confocal microscope, a SPIM microscope, and a multiphoton microscope, while all of these three categories of microscopes can also be used in an operational mode where the resolution is increased by optional modification due to adding an STED beam, therefore resulting in total in six different operational modes.

From a software perspective, it is also possible to separate the data detected by the camera 16 into lines and pixels and to generate simultaneously a SPIM image and a multiphoton image. This even allows dispensing with switching between SPIM mode and multiphoton mode, or in the alternative the simultaneous operation in the SPIM mode and in the multiphoton mode can be added as a switching option.

Summarizing, the microscope according to the invention applies a partial aspect of confocal microscopy, namely the partial aspect of the illumination optics, for generating an image based on the SPIM-technology, wherein the illumination optics is further modified to a zoom optics. According to the invention, further a confocal image can be generated that is one dimension lower than the image generated by the SPIM technology, or in the alternative in addition to the confocal image a multiphoton image can be generated, also in lieu of the image generated by the SPIM technology. This does not only allow to influence the image generated by the SPIM technology much more flexibly but allows also for additional image information obtained confocally or by multiphoton detection, and depending on the specific application, the resulting images can also be combined as an overlay with the SPIM and/or the multiphoton images. By adding or by turning off a STED beam the image can be influenced further and it is possible to generate even additional data streams for a variety of images, which further have the advantage of being generated simultaneously. This allows for providing the microscope with a manifold utility with synergistic effects in the possibilities of modulating the image and at the same time in the number of analyzable image information.

What is claimed is:

1. A STED-SPIM-microscope comprising:
 a light source sending an excitation light beam from a y-direction onto an object to be imaged;
 a camera detecting in a z-direction as a first detection direction light emanating from the object as at least one of fluorescent light and reflected light, wherein the z-direction extends substantially perpendicular to the y-direction;

a first x-scanner generating a sequential light sheet by scanning the excitation light beam in an x-direction, wherein the x-direction extends substantially perpendicular to the y-direction and to the z-direction and the light sheet is sequentially formed in a plane that is defined by the x-direction and the y-direction;

a deactivation light source sending from the y-direction via the first x-scanner that is a joint scanner for the excitation light beam and deactivation light beam at least one deactivation light beam that is scanned in x-direction onto the object making the effective sequentially generated light sheet that is generated by scanning the excitation light beam in the x-direction thinner in the z-direction, wherein the deactivation light beam has an intensity maximum that is at least offset in the z-direction in relation to the excitation light beam; and a deactivation light beam modulator having a structure that modulates the deactivation light beam to a cross-sectional shape that comprises in z-direction at least two intensity maxima with a zero point in between that is provided in the center of the excitation light beam.

2. The STED-SPIM-microscope according to claim 1, further comprising a phase plate that has a structure that modulates the deactivation light beam.

3. The STED-SPIM-microscope according to claim 1, further comprising an excitation light beam modulator that has a structure that modulates the excitation light beam to a Bessel beam.

4. The STED-SPIM-microscope according to claim 3, wherein the excitation light beam modulator is a Tunable Acoustic Gradient Index of Refraction (TAG) lens.

5. The STED-SPIM-microscope according to claim 3, wherein the excitation light beam modulator is an Axicon.

6. The STED-SPIM-microscope according to claim 1, further comprising at least one Acoustical Optical Element that has a structure that modulates at least the excitation light beam.

7. The STED-SPIM-microscope according to claim 6, wherein the Acousto Optical Element is an Acousto Optical Deflector (AOD).

8. The STED-SPIM-microscope according to claim 6, wherein the Acousto Optical Element is an Acousto Optical Tunable Filter (AOTF) for adjusting the frequency and the intensity of the excitation light beam.

9. The STED-SPIM-microscope according to claim 6, wherein the deactivation light beam comprises a constant frequency.

10. The STED-SPIM-microscope according to claim 1, further comprising at least one intensity controller that has a structure that adjusts the intensities of the excitation light beam and of the deactivation light beam.

11. The STED-SPIM-microscope according to claim 10, wherein the intensity controller comprises an Acousto Optical Element.

12. The STED-SPIM-microscope according to claim 1, wherein the deactivation light beam modulator is a Tunable Acoustic Gradient Index of Refraction (TAG) lens.

13. The STED-SPIM-microscope according to claim 1, wherein the deactivation light beam modulator is a Spatial Light Modulator (SLM).

14. The STED-SPIM-microscope according to claim 1, further comprising a switch that has a structure that switches between a first operational mode that is the normal SPIM mode without adding the deactivation light beam and a second operational mode that is a SPIM-plus-STED-mode where the deactivation light beam is in addition turned on.

15. The STED-SPIM-microscope according to claim 14, wherein the switch has a structure that makes a permanent selection between said first and second operational modes.

16. The STED-SPIM-microscope according to claim 14, wherein the switch has a structure that switches automatically at a specific switching frequency between said first and second operational modes.

17. The STED-SPIM-microscope according to claim 16, further comprising an image processing unit that separates the detected light detected by the camera in a first detection direction according to the first and second operational mode with the switching frequency into two data streams and generates simultaneously an image according to the first operational mode and an image according to the second operational mode.

18. The STED-SPIM-microscope according to claim 1, further comprising an illumination optics comprising an optical zoom that is provided in the beam path of the excitation light beam and comprises lens groups that are moved mechanically with respect to each other for varying the numerical aperture and therefore expanding or shortening the focus of the sequentially generated light sheet, therefore expanding or shortening the length of the field in the y-illumination direction that is illuminated by the light sheet within the object.

19. The STED-SPIM-microscope according to claim 1, further comprising a photodetector detecting fluorescent and/or reflected detection light emanating from the object into a second detection direction that is opposite to the y-direction.

20. The STED-SPIM-microscope according to claim 19, wherein in parallel to the 2-dimensional wide field image that is detected in the z-direction by applying the SPIM technology, also confocally a 1-dimensional image of the object is generated that is a line extending in the x-direction.

21. The STED-SPIM-microscope according to claim 19, further comprising a z-scanner moving the object in the z-direction so that sequentially a plurality of light sheets spaced in z-direction with respect to each other are generated in the respective illumination planes, wherein a distance between the respective light sheets and the camera remains unchanged.

22. The STED-SPIM-microscope according to claim 19, further comprising a switch that has a structure that switches between the following operational modes:
  i) confocal detection of detection light opposite to the y-excitation direction;
  ii) SPIM detection of wide field detection light in the z-direction;
  iii) multiphoton detection of wide field detection light in the z-direction;
  iv) simultaneous detection of the aforementioned confocal detection and spin detection; and
  v) simultaneous detection of the aforementioned confocal detection and multiphoton detection.

23. The STED-SPIM-microscope according to claim 19, wherein the operational modes i)-v) can optionally be established with or without additionally turning on the STED deactivation beam.

* * * * *